US00PP15302P2

(12) United States Plant Patent
Stephenson

(10) Patent No.: US PP15,302 P2
(45) Date of Patent: Nov. 9, 2004

(54) ***POLYGONATUM* PLANT NAMED 'KELLI'S GOLD'**

(50) Latin Name: *Polygonatum biflorum*
Varietal Denomination: Kelli's Gold

(76) Inventor: Theodore Lynn Stephenson, 5770 Hackman Ave. NE., Fridley, MN (US) 55432

( * ) Notice: Subject to any disclaimer, the term of this patent is extended or adjusted under 35 U.S.C. 154(b) by 0 days.

(21) Appl. No.: 10/672,749

(22) Filed: Sep. 27, 2003

(51) Int. Cl.[7] ..... A01H 5/00
(52) U.S. Cl. ..... Plt./263
(58) Field of Search ..... Plt./263

*Primary Examiner*—Kent Bell
(74) *Attorney, Agent, or Firm*—Penny J. Aguirre

(57) ABSTRACT

A new cultivar of *Polygonatum biflorum* 'Kelli's Gold' characterized by its golden yellow foliage and its ability to maintain its foliage coloration and vigor when grown under bright shady conditions.

2 Drawing Sheets

Genus and species: *Polygonatum biflorum.*
Cultivar: 'Kelli's Gold'.

BACKGROUND OF THE INVENTION

The present invention relates to a new and distinct cultivar of *Polygonatum biflorum* and will be referred to hereafter by its cultivar name, 'Kelli's Gold'. 'Kelli's Gold' represents a new Solomon's seal, an herbaceous perennial grown for landscape use.

The inventor collected and sowed seed from various unnamed plants of *Polygonatum biflorum* in 1989. 'Kelli's Gold' was selected from within a population of seedlings that were grown out from the seed collected from the unnamed plants of *Polygonatum biflorum* in Brookings, S.D. in the summer of 1990.

The new Solomon Seal was selected for its golden yellow foliage coloration. This characteristics makes this new cultivar unique and unlike any other known cultivars of *Polygonatum biflorum* known to the inventor.

Asexual reproduction of the new cultivar was first accomplished by rhizome division in Brookings, S.D. in spring of 1992 by the inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Kelli's Gold' as unique from all other selections and forms of *Polygonatum biflorum* known to the inventor.

1. Foliage is yellow in color and the coloration is maintained throughout the growing season. Foliage color is less yellow in heavier shade and on foliage that is basal and shaded by upper foliage.
2. Growth rate and foliage color is maintained in bright shade.
3. Vigorous growing rate once roots are established.
4. Tolerant to heavy clay soils.
5. Hardy to at least Zone 4.
6. Grows to a height of 45 to 60 cm (18 to 24 in).

7. Greenish-white flowers develop in late spring and bloom for about three weeks, followed by blue-black berries in summer.

BRIEF DESCRIPTION OF THE DRAWING

The plants and plant parts in the Figures depict a three-year-old plant in a three-gallon container as grown from a single rhizome division of 'Kelli's Gold' in Brookings, S.D. The plant was grown outdoors in bright shade.

Figure One is a digital photograph illustrating the foliage coloration when in peak bloom.

Figure Two is a digital photograph showing a close-up of the flowers.

The colors in the photographs are as close as possible while utilizing digital photography.

BOTANICAL DESCRIPTION OF THE PLANT

The following is a detailed description of the new cultivar as grown in a three-gallon container as grown for three years from a single rhizome division of 'Kelli's Gold' in Brookings, S.D. The phenotype of the new cultivar may vary with variations in environmental, climatic, and cultural conditions, as it has not been tested under all possible environmental conditions. The color determination is in accordance with the 2001 RHS Colour Chart of The Royal Horticultural Society, London, England, except where general color terms of ordinary dictionary significance are used.

Botanical classification: 'Kelli's Gold' is a cultivar of *Polygonatum biflorum.*
Commercial Classification: Solomon's seal.
Parentage: Seedling from seeds collected from unnamed plants of *Polygonatum biflorum.*
General description:

*Blooming period.*—About 3 weeks in late spring.

*Plant habit.*—Herbaceous rhizomatous, clump-forming perennial. Habit is upright to pendant with flowers arising on one side of the stems.

*Height and spread.*—Up to about 60 cm (24 in) in height and about 30 cm (12 in) width in two seasons from a single rhizome division.

*Hardiness.*—Tested to Zone 4.

*Culture.*—Grows best in moist, well-drained soil in partial shade. Tolerates drier soils once established and full sun in sufficiently moist soils. Tolerant to heavy clay soils once established.

*Diseases and pests.*—*Polygonatum biflorum* is relatively disease free. No susceptibility or resistance to diseases or pests has been observed for 'Kelli's Gold'.

*Root description.*—Fleshy roots arising from knotty rhizomes.

Growth and propagation:

*Propagation.*—Rhizome division.

*Time required for root development.*—Six weeks to fully develop from a single rhizome division in a one-quart container in soil-less media when grown at 70–80° F. in a greenhouse without supplemental lighting in summer.

Stem description:

*Shape.*—Round, solid.

*Stem color.*—Basal portion and in lower light conditions 144B, distal segments and in higher light condition (supporting more golden foliage) N144B.

*Stem size.*—Approximately 2 to 4 mm in diameter, up to about 50 cm in length.

*Stem surface.*—Glabrous.

*Branching.*—Caulescent. No secondary branches, all stems arise from rhizomes.

Internode length.—1 to 3.5 cm.

Foliage description:

*Leaf shape.*—Broadly elliptic.

*Leaf division.*—Simple.

*Leaf base.*—Rounded.

*Leaf apex.*—Acuminate.

*Leaf venation.*—Parallel to leaf margins. Slightly recessed on upper foliage, color matching the color of foliage with basal region of lighter foliage, 144C.

*Leaf margins.*—Entire.

*Leaf attachment.*—Sessile.

*Leaf arrangement.*—Alternate.

*Leaf surface.*—Upper; glabrous. Lower; slightly glaucous with minute hairs.

*Leaf color.*—Immature and mature at lower light levels: upper; 147A, lower; 138B.

*Mature at higher light levels.*—Upper and lower; primarily 1C suffused with 144C (primarily in basal regions and midribs), changing to 1A in high light and 1D in full sun or dry conditions.

*Leaf size.*—4 to 7 cm in length, 2 to 4.5 cm in width.

*Leaf quantity.*—Up to about 18 per stem.

Flower description:

*Inflorescence type.*—Pendent, cymose clusters of tubular flowers.

*Lastingness of inflorescence.*—Determinate, blooms last approximately 3 weeks.

*Flower fragrance.*—None.

*Perianth form.*—Tubular, comprised of 6 fused tepals with distal 3 mm portion unfused to create an aperture of about 3 mm when fully open.

*Flower aspect.*—Downward on pendant peduncles.

*Flower size.*—About 1.2 to 1.5 cm in depth, about 6 to 7 mm in width. Short tube at base is about 1.5 mm in length, about 1 mm in width.

*Flower number.*—2 to 3 per leaf node, up to about 25 per flowering stem.

*Flower color.*—Upper and lower surfaces of tepals: 1C with darker tips and bases of 144B.

*Flower surface/appearance.*—Waxy.

*Tepal size.*—About 1.2 to 1.5 cm in length, width not measurable due to fusion of tepals.

*Tepal apex.*—Acute, about 2 to 3 mm of distal region of tepals is unfused when flower is fully open.

*Tepal margin.*—Fused, entire on unfused region.

*Buds.*—144B in color, up to 1.3 cm in length, up to 7 mm in width.

*Bud shape.*—Oblong.

*Peduncle.*—Arises from leaf node at center of leaf, about 2 cm in length, about 1 mm in width, 151A in color, waxy surface, 1 per leaf node.

*Pedicels.*—2 to 3 per peduncle, about 5 to 7 mm in length, about 1 mm in width, 151A in color, waxy surface.

Reproductive organs:

*Gynoecium.*—1 Pistil, 1.3 cm in length and 5 mm in width, 1C in color (style and stigma). Ovary is superior, 1-locular, 3 mm in length and 2 mm in width, 14C in color.

*Androcoecium.*—6 stamens. Filaments are papillose, adnate to tepals, 7 cm in length, 1.5 mm in width and 1C in color. Anthers are 8B in color, attachment is versatile. Pollen is moderately abundant, very fine and 8D in color. Dehiscence is longitudinal.

*Fruit.*—Globose berry, present in late summer, about 1 to 1.4 cm in diameter, color is 136A with shades of 136B turning blue-black on maturity (103A, slightly more black), glaucous surface, flesh color is 146C.

*Seeds.*—18B in color, about 12 in quantity, about 4 to 5 mm in diameter, basically round in shape with one side flattened.

I claim:

1. A new and distinct cultivar of *Polygonatum* plant named 'Kelli's Gold' substantially as herein illustrated and described.

* * * * *

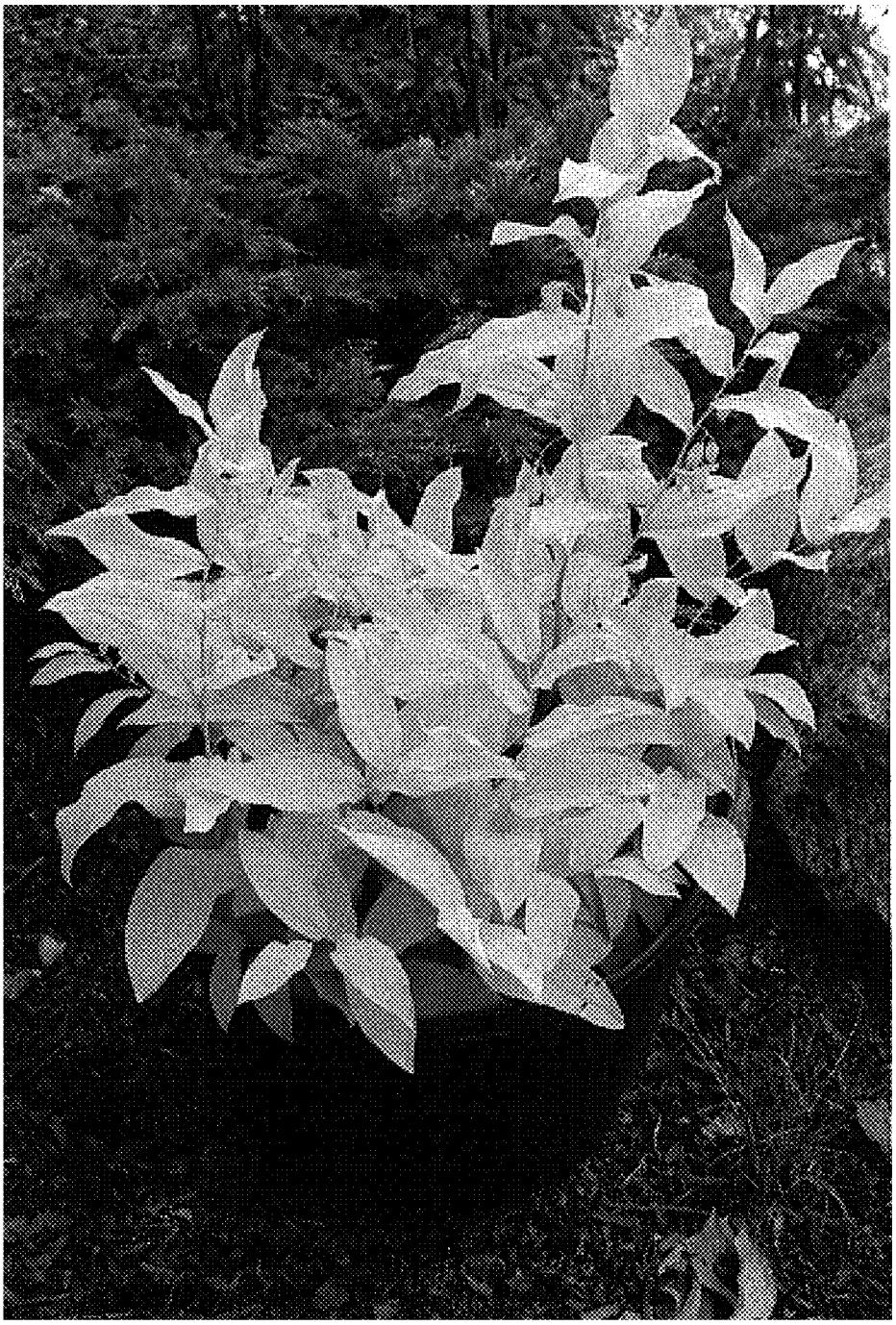
Figure One

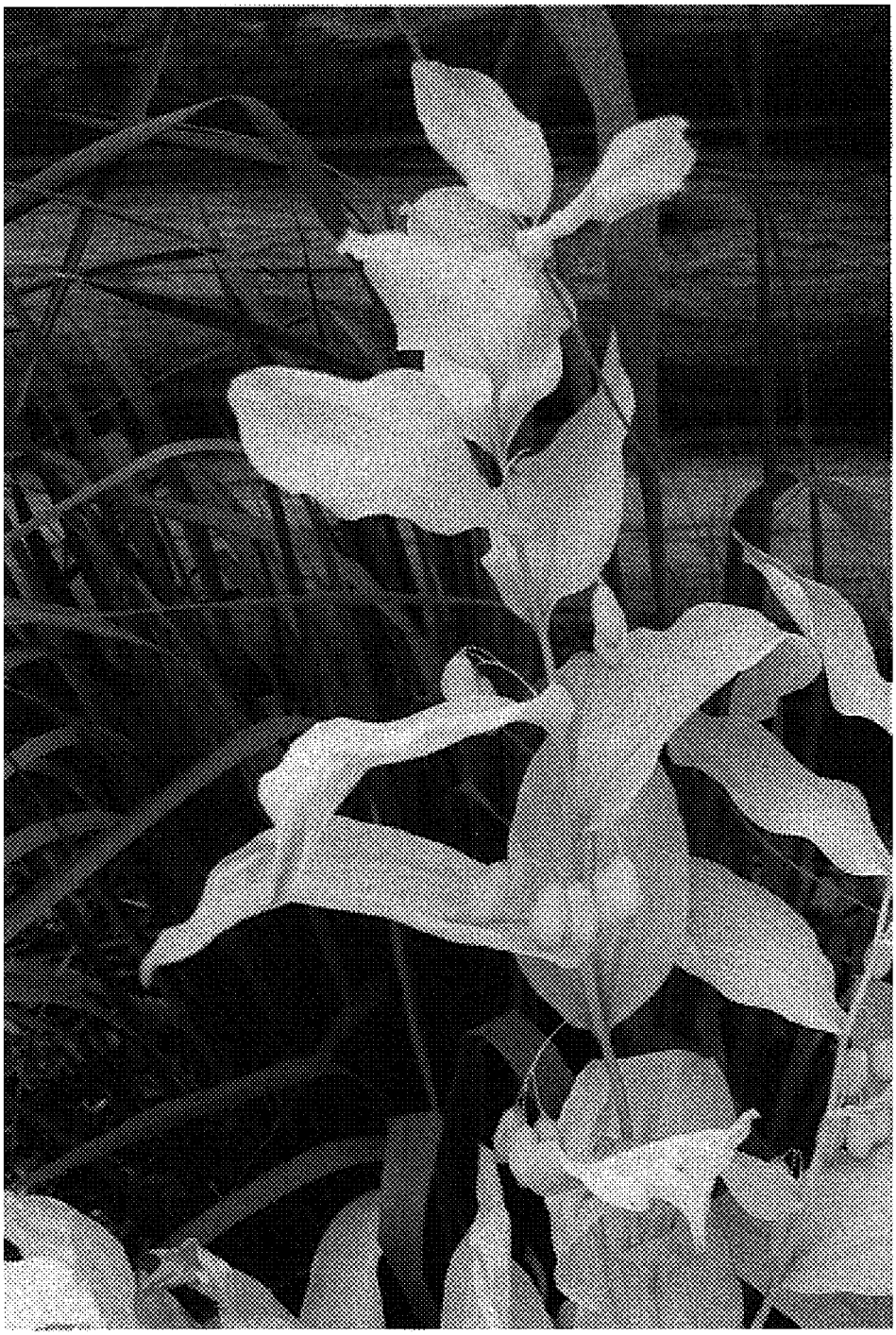
Figure Two